United States Patent [19]
Clement

[11] Patent Number: 5,176,642
[45] Date of Patent: Jan. 5, 1993

[54] VACUUM POWDERED SYRINGE

[75] Inventor: Thomas P. Clement, Bloomington, Ind.

[73] Assignee: Mectra Labs, Inc., Bloomfield, Ind.

[21] Appl. No.: 667,665

[22] Filed: Mar. 11, 1991

[51] Int. Cl.⁵ .............................................. A01M 5/00
[52] U.S. Cl. ..................................... 604/135; 604/141
[58] Field of Search ............... 604/135, 134, 141, 143, 604/147, 152, 27, 28, 35

[56] References Cited

U.S. PATENT DOCUMENTS

| | | |
|---|---|---|
| 577,682 | 2/1897 | Eissner . |
| 686,332 | 11/1901 | Prescott . |
| 840,472 | 1/1907 | Brookes . |
| 1,343,085 | 6/1920 | Lerch . |
| 1,736,573 | 3/1927 | Besse . |
| 1,898,435 | 2/1933 | Fillauer . |
| 2,101,104 | 3/1935 | Hege . |
| 2,545,017 | 3/1951 | Billingsley . |
| 3,635,218 | 1/1972 | Ericson . |
| 3,688,765 | 9/1972 | Gasaway . |
| 3,699,961 | 10/1972 | Szpur . |
| 3,815,481 | 6/1974 | Pauliukonis . |
| 3,818,907 | 6/1974 | Walton . |
| 3,828,778 | 8/1974 | Weinhart . |
| 3,840,007 | 9/1972 | Fish . |
| 3,949,748 | 4/1976 | Malmin ............................. 604/135 |
| 4,030,498 | 6/1977 | Tompkins . |
| 4,036,232 | 7/1977 | Genese . |
| 4,124,024 | 11/1978 | Schwebel et al. . |
| 4,245,654 | 1/1981 | Raitto . |
| 4,315,506 | 2/1982 | Kayser et al. ..................... 604/135 |
| 4,361,155 | 11/1982 | Anastasio . |
| 4,421,508 | 12/1983 | Cohen . |
| 4,515,591 | 5/1985 | Hemmerich et al. . |
| 4,648,870 | 3/1987 | Goldberg et al. ................... 604/135 |
| 4,662,868 | 5/1987 | Cambio, Jr. . |
| 4,684,366 | 8/1987 | Denny et al. . |
| 4,705,509 | 11/1987 | Stade . |
| 4,766,908 | 8/1988 | Clement . |

FOREIGN PATENT DOCUMENTS

| | | |
|---|---|---|
| 2706303 | 4/1978 | Fed. Rep. of Germany . |
| 194878 | 3/1965 | Sweden . |
| 791376 | 12/1980 | U.S.S.R. ............................. 604/143 |
| 624958 | 6/1949 | United Kingdom .............. 604/143 |
| 9106338 | 5/1991 | World Int. Prop. O. ........... 604/143 |

Primary Examiner—Paul J, Hirsch
Attorney, Agent, or Firm—Barnes & Thornburg

[57] ABSTRACT

A medical apparatus for injecting or withdrawing biological or therapeutic fluid includes a syringe body defining a syringe cavity into which fluids can be introduced or withdrawn by way of a fluid port and a vacuum port. A piston is positioned for reversible movement in the syringe cavity between the fluid port and the vacuum port so that movement of the piston in response to a decrease in fluid pressure causes a resilient element positioned within the cavity to be compressed. The compressed spring provides a store of mechanical energy that can be used to drive the piston toward the fluid port and expel fluid contained in the first cavity through the fluid port when pressure within the syringe cavity is equalized. Control of vacuum and air inlet into the syringe cavity is conveniently controlled by a dual port valve connected to the syringe body.

24 Claims, 4 Drawing Sheets

VACUUM POWDERED SYRINGE

BACKGROUND AND SUMMARY OF THE INVENTION

The present invention relates to syringes for medical or veterinary uses and more particularly to the provision of semi-automatically powered disposable syringes for injection of fluids.

Hypodermic syringes for the injection of medicaments or aspiration of fluids are commonly hand operated. The amount of work required to operate such manual syringes can present difficulties for a syringe operator transferring large quantities of liquids during the course of an operation or when injecting large numbers of individuals. As the hand tires, consistent removal or injection of liquids at a constant rate is impeded. Another problem associated with manual syringes is the inability of syringe operators to inject or remove liquid at high rates due to the weakness of the hand or the high viscosity of the liquid to be injected.

To overcome the problems associated with manually powered syringes, mechanically powered syringes have been developed to provide aspiration or injection of liquids. For example, a positive pressure infusion pump of syringe type is described in U.S. Pat. No. 4,515,591 to Hemmerich et al., issued May 7, 1985. In the disclosed device, a syringe having a precise displacement volume is repeatedly filled and emptied on alternate syringe piston strokes during a combined fill and pump cycle. The piston reciprocating in the syringe is driven at a selected cyclic rate by a motor drive system. Another example of powered injection system is described in U.S. Pat. No. 4,596,556 to Morrow et al., issued Jun. 24, 1986. In that device, a needleless injection system is powered by a pressurized gas cartridge. When the gas in the cartridge is released, the expanding gas drives a plunger forward through the length of a syringe shell to expel liquid medication from the device.

However, mechanically driven syringes are not without problems. Typically, the rate of injection (or aspiration) is set in advance and cannot easily be altered while the syringe is in use. Positive controls are required to ensure that force driving the syringe is not in excess of what is required for injection or withdrawal of fluids. Failure of such positive controls on the rate of injection or withdrawal could result in tissue damage and injury to the patient.

To overcome problems associated with powered syringes, an apparatus for injecting fluids or providing aspiration is provided. This apparatus includes a syringe body formed to define a syringe cavity. The syringe body is formed to have a fluid port and a vacuum port for the introduction and withdrawal of fluids into the syringe cavity. A piston is positioned for movement in the syringe cavity between the fluid port and the vacuum port. Because of its position in the syringe cavity, the piston acts to define a first cavity within the syringe cavity positioned between itself and the fluid port and a second cavity within the syringe cavity positioned between itself and the vacuum port. In addition, the piston forms an airtight seal with the syringe body to prevent fluid communication between the first cavity and the second cavity. A resilient element is positioned in the second cavity of the syringe cavity to connect between the piston and a base that is immovable with respect to the piston. Movement of the piston toward the vacuum port in response to a decrease in the fluid pressure of fluid contained in the second cavity relative to the fluid pressure of fluid contained in the first cavity deforms the resilient element to provide a store of useful mechanical energy. This useful mechanical energy can be released by operating an air inlet valve controllable to admit air into the second cavity. This equalizes the fluid pressures in the first and second cavities and enables release of the store of useful mechanical energy contained in the resilient element as the resilient element returns to its original configuration and consequently drives the piston toward the fluid port. The movement of the piston expels fluid contained in the first cavity through the fluid port.

Although in preferred embodiments a conventional disposable syringe body and piston is used to transfer fluids into or out of the body, the present invention is not limited to the use of such conventional syringes. More generally, the present invention is directed to an apparatus for dispensing fluids that includes a chamber formed to define a cavity and a movable element disposed in the cavity to divide the cavity into first and second cavities having predefined volumes. The first and second cavities are accessible through first and second apertures to permit fluid flow into and out of the respective first and second cavities. In operation, the second cavity initially is provided with a second fluid, typically air at normal atmospheric pressure. To draw fluid into the first cavity, removing means for removing at least a portion of the second fluid from the second cavity through the second aperture is utilized to promote movement of the movable element in the cavity of the chamber in such a manner as to reduce the volume of the second cavity and increases the volume of the first cavity. The reduction of fluid pressure in the first cavity acts to draw fluid into the first cavity through the first cavity aperture. As the movable element moves through the syringe cavity, storage means for storing energy produced by movement of the movable element in response to removal of at least a portion of the second fluid from the second cavity is actuated. This storage means is connected between the movable element and a base that is substantially immobile relative to the movable element. The controlled release of the energy contained in the storage means is initiated by actuation of an equalizing means for equalizing fluid pressure in the first and second cavities. The energy so released is used to promote movement of the movable element in the cavity of the chamber to reduce the volume of the first cavity and increase the volume of the second cavity, so that fluid contained in the first cavity is expelled from the first cavity, and the volume of the second cavity is brought back to its predetermined starting volume before movement of the movable element.

The present invention also comprises a method for injecting fluids. Steps of the method include providing a chamber defining a cavity, the cavity being divided into first and second cavities by a divider situated to prevent fluid communication between the first and second cavities. Reducing pressure in the second cavity to create a pressure imbalance between fluid in the first cavity and fluid in the second cavity results in storing energy in an amount less than or equal to a predetermined amount that is a function of the pressure imbalance. Equalizing the pressure imbalance between the fluid in the first cavity and the fluid in the second cavity and applying the stored energy against the divider to decrease the volume of the second cavity acts to expel fluid contained in the first cavity.

In preferred embodiments of the present invention, the air inlet valve is configured to form a handheld disposable valve having connections to both a vacuum source and to the atmosphere. The valve has three operating positions. In a first position the vacuum port entering into the second cavity of the syringe body is in open fluid communication with the vacuum source (typically a vacuum line attached to a vacuum chamber or vacuum pump) to promote the withdrawal of fluid contained in the second cavity through the valve and into the vacuum source. As a result of the application of the vacuum, fluid is drawn into the expanding first cavity and the resilient element is deformed in a manner calculated to store useful mechanical energy. When the desired fluid pressure within the second cavity is reached, the valve can be moved to a closed position. This closed position can be maintained as long as desired by the operator. Movement of the valve to its third position results in opening the second cavity of the syringe body to the atmosphere. Air can move into the area of reduced pressure and the resilient element adjusts its conformation to regain its original form. This adjustment in the shape of the resilient element can be used to provide a force sufficient for driving a piston, diaphragm, or other movable element in a manner calculated to expel fluid contained in the first cavity through the fluid port.

In other preferred embodiments the resilient element includes a compressible spring positioned within the second cavity of the syringe. This spring provides a mechanical connection between a movable element such as a piston and a base that is substantially immovable relative to the movable element. Movement of the movable element, piston, diaphragm, or other divider of the syringe cavity in a direction that reduces the volume of second cavity in response to withdrawal of air from the second cavity will also act to deform (by compression in this instance) the spring. When the deforming force is released by actuation of an air inlet valve, substantially the same amount of mechanical energy as required to maintain the degree of deformation of the spring is released in a direction suitable for driving the movable element through the syringe cavity to reduce the volume the first cavity and expel any fluid contained in the apparatus out through a fluid port.

DETAILED DESCRIPTION OF THE DRAWINGS

Figure 1:
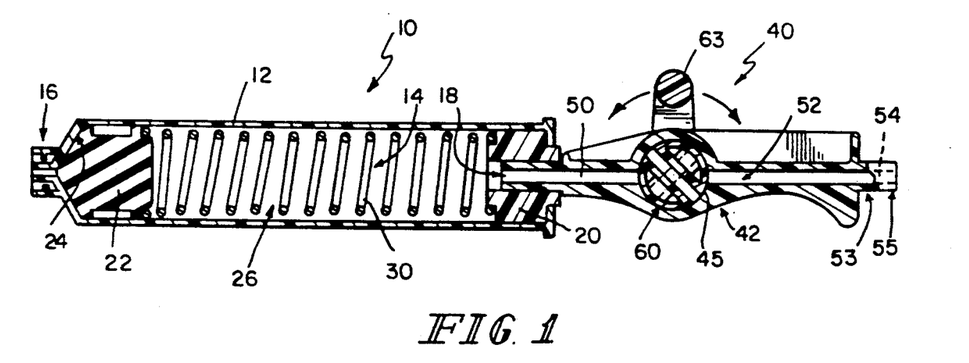
FIG. 1 is a perspective view of an apparatus for injecting or withdrawing fluids in a normally closed position, with a spring positioned in a second cavity of a syringe to hold a piston adjacent to a fluid port defined in the syringe.
Figure 2:
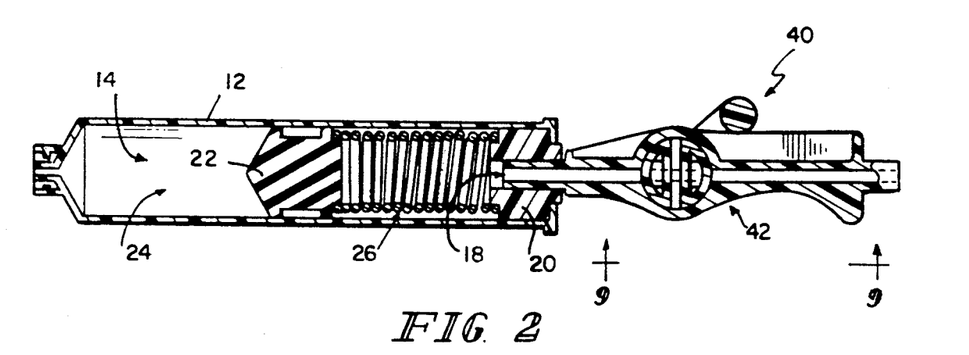
FIG. 2 is a perspective view of the apparatus shown in FIG. 1, with a rotor rotated to a first position that connects the second cavity in fluid communication with a vacuum source to evacuate the cavity and cause compression of the spring contained therein by movement of the piston toward a vacuum port.
Figure 3:
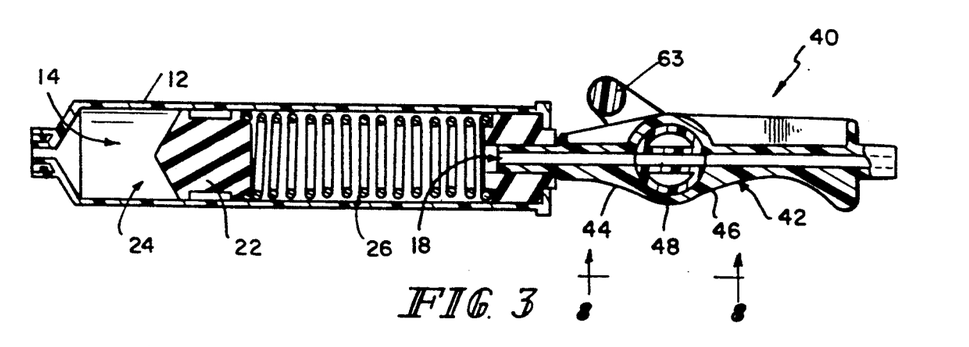
FIG. 3 is a perspective view of the apparatus shown in FIGS. 1 and 2, with the rotor moved to a second position that places the second cavity in fluid communication with air to equalize the pressures in the second cavity and a first cavity and allow expansion of the spring to move the piston toward the fluid port to expel any contained fluid.

As illustrated in FIGS. 1-3, a vacuum powered syringe 10 consists of a standard disposable syringe body 12 defining a syringe cavity 14. The syringe cavity 14 can be accessed through both a fluid port 16 and vacuum port 18. The fluid port 16 can be fitted with a variety of surgical needles, tubing, or other medical equipment (not shown) for transferring fluids as desired. The vacuum port 18 is defined by an annular plug 20 permanently attached to the syringe body 12.

Positioned inside the syringe cavity 14 is a piston 22 that divides the syringe cavity 14 into a first cavity 24 positioned between the piston 22 and the fluid port 16 and a second cavity 26 positioned between the piston 22 and the vacuum port 18. The piston 22 is formed from a slightly resilient material and dimensioned to form an airtight seal with the syringe body 12. The piston 22 can slidingly move within the syringe cavity while maintaining this airtight seal with the syringe body 12. Movement of the piston 22 toward the vacuum port 18 (as generally shown in FIG. 2) acts to decrease the volume of the second cavity 26 as the volume of the first cavity 24 increases. Movement of the piston in the opposite direction toward the fluid port 16 (as generally shown in FIG. 3) acts to decrease the volume of the first cavity 24 as the volume of the second cavity 26 increases.

A spring 30 is positioned within the second cavity 26 to extend between the plug 20 of the syringe body 12 and the piston 22. The spring 30 is formed from resilient spring steel into a helical shape and biased to exert a continuing force against the piston 22. This force pushes the piston 22 to lie adjacent to the fluid port 16, minimizing the volume of the first cavity 24 and maximizing the volume of the second cavity 26. Movement of the piston 22 toward the vacuum port 18 will elastically deform the spring 30 from its initial shape, compressing the spring 30 and storing an increasing amount of mechanical energy substantially proportional to the distance of the piston 22 from the vacuum port 18. Accordingly, the closer the piston 22 approaches the vacuum port 18, the proportionately greater amount of energy stored (in the form of elastic deformation) in the spring 30. It will be appreciated by those skilled in the art that helical springs are only one means of storing the energy provided by movement of the piston 22. Alternatively, other types of resilient elements such as leaf springs, cantilevers, elastomeric foams or rubbers, compressed gasses, or any other type of element or system that tends to return to its initial state upon the release of a deforming force (the force can be compressive, in tension, or a combination of both) can be used to store energy for later release to drive the piston 22 toward the fluid port 16.

A dual port valve 40 is connected to the syringe body 12. The valve 40 includes a valve body 42 formed to define a connecting passageway 50 situated in fluid communication with the second cavity 26 through the vacuum port 18. A vacuum inlet 52 terminating in a nipple 53 suitable for connection with a vacuum hose leading to a vacuum source (vacuum hose and vacuum source not shown in Figs.) and an air inlet 54 terminating in a nipple 55 are also defined in the valve body 42.

Fluid flow within the connecting passageway 50 is controlled by movement of a rotor 60 situated in a cylindrical opening 45 defined by the valve body 42. The cylindrical opening 45 extends completely through the valve body 42 to respectively intercept the connecting passageway 50, the vacuum inlet 52, and the air inlet 54. The rotor 60 is formed to define a first valve passageway 62 and a second valve passageway 64 that extend through the rotor 60 at predefined skew angles relative to each other. The rotor 60 is positioned within the cylindrical opening in snug slidable fit so that it can be rotated into a first valve position (shown in FIG. 2) with the first valve passageway 62 brought into a position that allows fluid communication between second cavity 26, the connecting passageway 50, the first valve passageway 62, the vacuum inlet 52, and the nipple 53. Connection of the nipple 53 to a vacuum source allows withdrawal of fluid from the second cavity 26. Generally the fluid contained in the second cavity 26 will be air at normal atmospheric pressure, but liquids or other types of gasses could also be present if desired.

Figure 8:
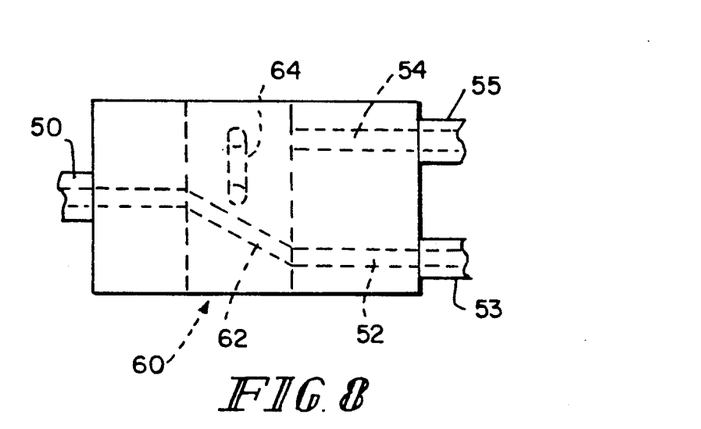
Figure 9:
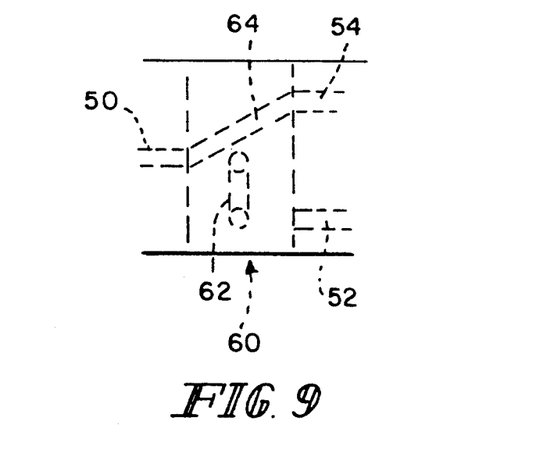

Admission of air (or other fluids) into the second cavity 26 is achieved by rotating the the rotor 60 into a second valve position (shown in FIG. 3 and FIG. 8) that brings the second cavity 26 into fluid communication with the connecting passageway 50, the second valve passageway 64, the air inlet 54, and the nipple 55. If the fluid contained in the first cavity 24 is maintained at normal atmospheric pressure, movement of the rotor 60 to its second valve position acts to equalize fluid pressures in the first cavity 24 and second cavity 26.

The rotor 60 can be rotated to closed position intermediate to its first and second valve position (shown in FIG. 1). In this closed position, the connecting passageway 50 is not in fluid communication with either the first valve passageway 62 or the second valve passageway 64. There is no fluid movement either into or out of the second cavity 26 when the rotor is positioned in the closed position.

To permit snug slidable movement of the rotor 60 between first, second, and closed valve positions, the valve body 42 is preferably be molded from a rigid material such as a polycarbonate plastic while rotor 60 may preferably be molded from a softer plastic such as a polypropylene, nylon or teflon. The closeness of the snug fit of the rotor 60 in the cylindrical opening 45 and the nature of the material from which the valve body 42 and rotor 60 are molded determines the pressure capacity of the valving mechanism. It will be appreciated that a very snug rotor 60 fit in the cylindrical opening 45 will accommodate the differential pressure created between the second cavity and normal atmospheric pressure when a vacuum is drawn to evacuate the second cavity 26 through the valve body 42 and attached rotor 60.

For convenience in operation, the dual port valve 40 has several features that increase ease of use. For example, the valve body 42 is configured to be manually grippable for ease of operation. The valve body 42 is formed to provide a forward bottom portion 44 shaped to be gripped by the index finger of one hand and a rearward bottom portion 46 shaped to be gripped by the middle finger and, depending upon the size of the hand, by the fourth finger of the hand, with a depending central portion 48 between the forward and rearward portions 44, 46. The recessed portions 44, 46 are smoothly transversely recessed for gripping comfort while the depending central portion 48 is smoothly rounded to fit between the index and middle fingers. It will further be appreciated that the the valve mechanism 40 and the valve body 42 are proportioned and shaped to be held by the index and middle fingers of an adult's hand so that the valve body 42 is pressed against the palm of the hand, leaving the thumb free. The rotor 60 is provided with a peripherally extending thumb engaging arm 63 integrally molded thereon that can be engaged by this free thumb. The thumb engaging arm 62 extends generally parallel to and above the rotor 60. This engaging portion 63 may be serrated to provide a gripping surface for the thumb. As shown in the Figs., this actuating or engaging arm 63 is integrally molded with the rotor 60, but it can alternatively be constructed from a separate piece fixedly attached to the rotor 60. For control purposes, the arm 63 connected to the rotor 60 should have a moment-arm of approximately one inch and a stroke of approximately three-fourths inch, a comfortable span for either an adult female or male hand.

In operation, the nipple 53 terminating the vacuum inlet 52 of the dual port valve 40 such as shown in FIG. 1 is connected to a vacuum source (not shown) such as is commonly available in hospitals or other medical treatment centers. Connection to the vacuum source through a flexible vacuum hose (not shown) is generally most convenient, but rigid vacuum couplings may also be used. The nipple 55 of the air inlet 54 is generally not connected to any hosing, but is simply left in an unblocked position that permits entrance or exit of air at normal atmospheric pressure. However, it is of course possible to connect the nipple 55 to a fluid source (not shown) maintained at a pressure greater or less than atmospheric pressure. Generally, the fluid pressure within the second cavity 26, the first cavity 24, and normal atmospheric pressure of air surrounding the syringe 10 are substantially equivalent.

The fluid port 16 is then positioned in fluid contact with some fluid that the operator of the syringe 10 desires to draw into the first cavity 24. As shown in FIG. 2, the thumb engaging arm 63 integrally formed with the rotor 60 is rotated away from the syringe body 12. This action brings the vacuum inlet 52, the first valve passageway 62 defined in the rotor 60, the connecting passageway 50, and the second cavity 26 into fluid communication with each other. Because of the connection of the vacuum inlet 52 to a vacuum source, any air (or other fluid) contained in the second cavity 26 is withdrawn. Because of the airtight seal between the first cavity 24 and the second cavity 26, a differential pressure is created between the cavities 24, 26 as air is withdrawn from the second cavity 26. Fluid pressure against the piston 22 exerted by fluid contained in the first cavity 24 acts to drive the piston 22 toward the vacuum port 18, simultaneously diminishing the volume of the second cavity 26 and increasing the volume of the first cavity 24. The increase in volume of the first cavity 24 acts to draw fluid into the first cavity 24, filling that cavity 24 with the desired biological or therapeutic fluid. The decrease in volume of the second cavity 26 as the piston 22 advances through the syringe cavity 14 toward the vacuum port 18 results in the compression of the spring 30 between the piston 22 and the plug 20. As long as the elastic limit of the spring 30 is not exceeded, the spring 30 will store an amount of energy corresponding to the force (atmospheric pressure, approximately 760 torrs, $1.013 \times 10^5$ N/m$^2$) exerted by the fluid against the surface area presented by the piston 22. When this amount of energy is stored by the spring 30, advancement of the piston toward the vacuum port 18 ceases, and no more fluid is drawn into the first cavity 24.

An operator can release this stored energy in the spring 30 to drive the piston 22 toward the fluid port 16 simply by rotating the thumb engaging arm 63 integrally formed with the rotor 60 toward the syringe body 12. This brings the air inlet 54, the second valve passageway 64 defined in the rotor 60, the connecting passageway 50, and the second cavity 26 into fluid communication with each other. Air rushes through these passageways to fill the second cavity 26 with air at normal atmospheric pressure. This newly admitted air exerts a force directed against the piston 22 in the direction of the fluid port 16 substantially equivalent to the force exerted by fluid in the first cavity 24 against the piston 22 in the direction of the vacuum port. Since these fluid pressures are now balanced, the spring 30 is not opposed by the fluid pressure in cavity 24, permitting the deformed, compressed spring to rebound to its original shape before compression between the piston 22 and the plug 20. As the spring 30 expands, it drives the piston 22 toward the fluid port 16 with a force that is initially no greater than the force of atmospheric pressure, simultaneously diminishing the volume of the first cavity 24 and increasing the volume of the second cavity 26. The decrease in volume of the first cavity 24 acts to expel any contained fluid through the fluid port 16. The thumb engaging arm 63 of the rotor 60 can then be moved back to its closed position, bringing the configuration of the vacuum powered syringe 10 back to its original form as seen in FIG. 1, ready for reuse or disposal.

Figure 4:
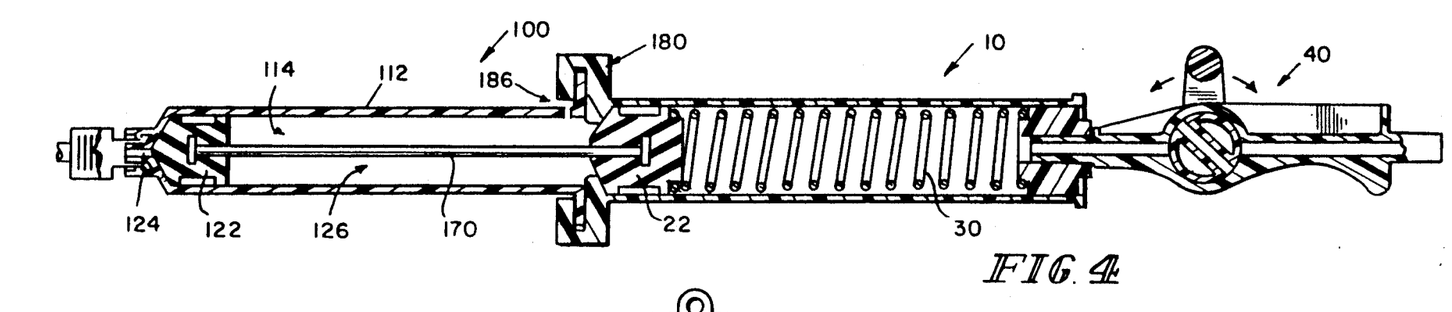
FIG. 4 is a perspective view of a viscous fluid injection system that includes a vacuum powered syringe such as is shown in FIGS. 1-3 connected to a smaller syringe to increase the mechanical advantage of the force exerted to expel viscous fluid initially contained in the second syringe.

Another embodiment of the invention is shown in FIG. 4. In FIG. 4, a viscous fluid injection system 100 is formed by combining a vacuum powered syringe 10 such as is shown in FIGS. 1-3, and syringe body 112 formed to have a syringe cavity 114 with a cross sectional area less than the cross sectional area of the syringe cavity 14. The syringe body 112 is connected to the vacuum powered syringe 10 with a connector 180 that rigidly holds these two units together. The connector further defines an air inlet 182 that connects the first cavity 24 in syringe cavity 14 in fluid communication with the atmosphere. A connecting rod 170 is used to connect the piston 22 positioned in the syringe cavity 14 and a piston 122 positioned within the syringe cavity 114.

In operation, the viscous fluid injector 100 is manipulated in exactly the same manner as the vacuum powered syringe 10, with the sole exception being substitution of the syringe cavity 124 in the syringe 112 for the syringe cavity 24 in the syringe 12. In the viscous fluid injector 100, fluid is drawn into and expelled from the syringe cavity 124 as the rod 170 respectively moves toward the vacuum powered syringe 10 and away from the syringe 10. Because of the differential surface presented by the pistons 122 and 22, a mechanical advantage proportional to that surface area differential can be used to drive extremely viscous fluids out from the syringe cavity 124. This allows the continued use of vacuum powered devices (that have a driving force limited by atmospheric pressure) to be utilized in conjunction with fluids that ordinarily require expulsive forces from a syringe greater than that provided by atmospheric pressure.

Figure 5:
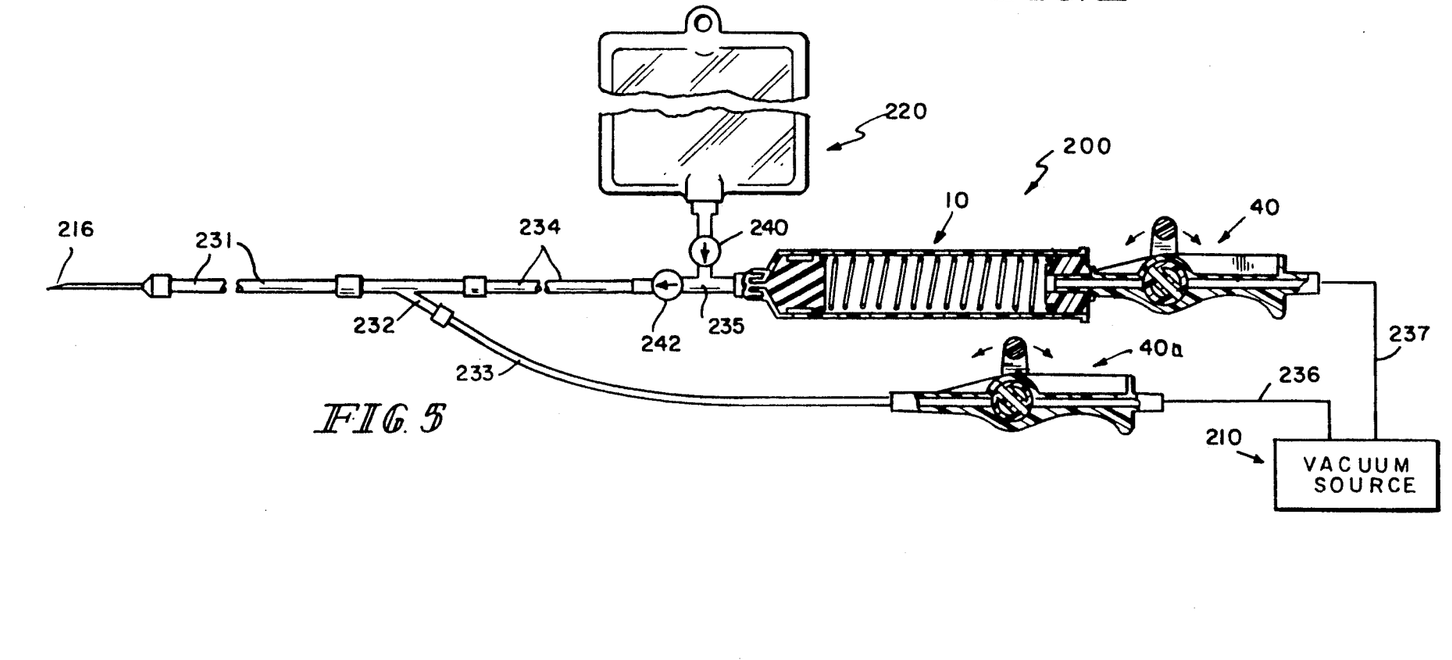
FIG. 5 is a side view of a vacuum powered syringe such as shown in FIGS. 1-3 forming part of an aspiration/injection system for introduction and withdrawal of fluids.

FIG. 5 illustrates a fluid transfer system 200 for introduction and aspiration of fluids. The system 200 utilizes a vacuum powered syringe 10 to drive the introduction of fluids. The system 200, which also includes a valve 40, a vacuum source 210, a fluid source 220, a fluid port 216, tubing 231, 232, 233, 234, and 235, vacuum lines 236 and 237, and one-way valves 240 and 242. The one-way valves 240 and 242 can be flap-type valves or any other conventional one-way valve that permits fluid flow only in the direction indicated by the arrow. The vacuum powered syringe 10 is powered by its connection to vacuum source 210 through vacuum line 237, and its fluid driving connection is provided by its connection to tubing 235. Tubing 235 is connected to the one-way valves 242 and 240. Valve 240 in turn is connected to the fluid source 220. The valve 242 is connected to tubing 234, which connects to tubing 232, 231, and has a fluid port at 216 through which fluid can enter or leave the tubing system. The tube 232 is also connected to tubing 233 which connects to a normally closed valve 40a. The valve 40a is also connected to the vacuum source 210 through the vacuum line 236.

In operation, fluid can be introduced into a patient by operating the vacuum powered syringe 10 as discussed in regard to FIGS. 1-3. Fluid will be drawn from the fluid source 220 through the one-way valve 240 into the syringe 10. When the desired amount of fluid has been drawn into the syringe 10 it can be expelled from the syringe 10 in a manner as previously described, moving through the one-way valve 242 into the tubing 234, 232, 231, and into the patient through the fluid port 216. If aspiration or withdrawal of fluid from a patient is desired, the valve 40a can be opened. This will cause movement of fluid into the fluid port 216 and through the tubing 231, 232, 233, and vacuum line 236.

Figure 6:
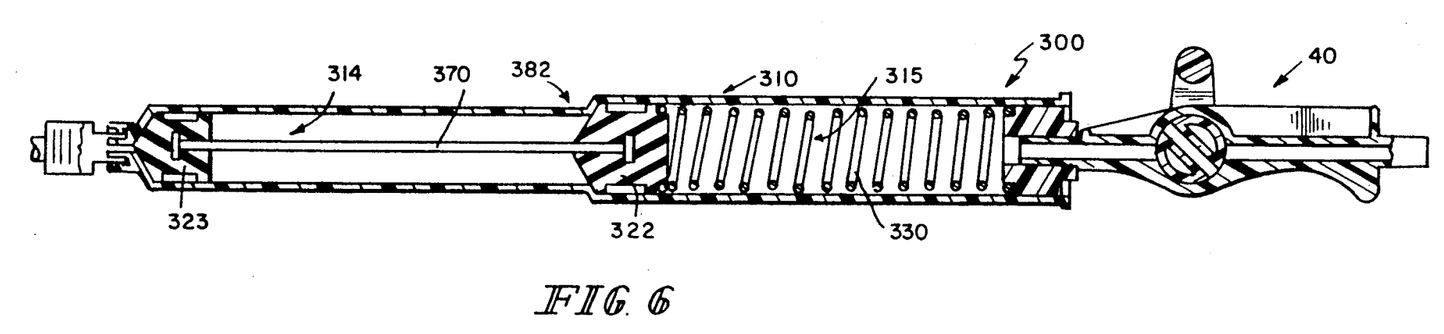
FIGS. 6 and 7 show a vacuum powered syringe having two chambers defined by a one-piece body configured to accommodate dual pistons interconnected by a rod and FIGS. 8 and 9 show details of the valve looking upward from below the valve along the line 8—8 in FIG. 3 and line 9—9 in FIG. 2.
Figure 7:
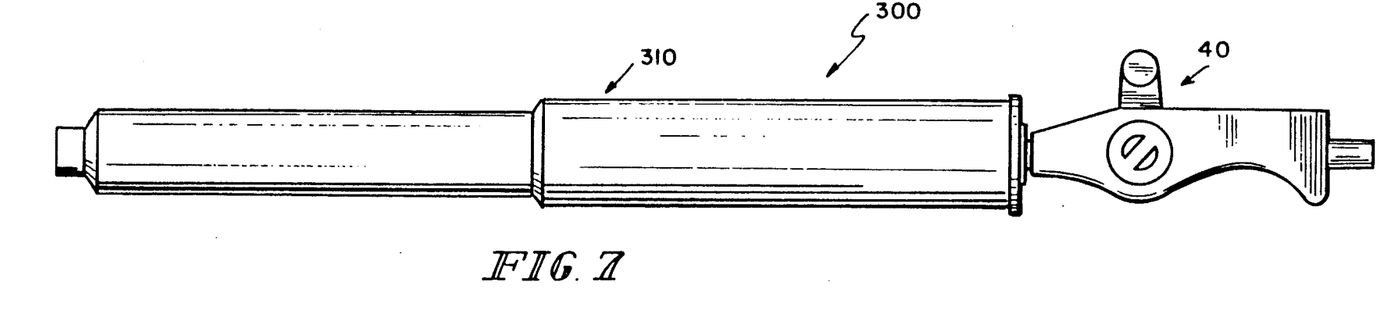

FIGS. 6 and 7 illustrate another embodiment of the invention similar to that shown in FIG. 4. In FIGS. 6 and 7, a viscous fluid injection system 300 is formed by combining a valve 40 with a one piece, molded plastic syringe body 310 internally configured to have a syringe cavity 314 with a cross sectional area less than the cross sectional area of a syringe cavity 315. An air inlet 382 permits admission of air at atmospheric pressure into the syringe cavity 314. A connecting rod 370 connects a piston 323 positioned in the syringe cavity 314 and a piston 322 positioned within the syringe cavity 315. Energy is stored for later release to drive pistons 322 and 323 by a spring 330 positioned in the syringe cavity 315. This embodiment of the invention can be operated in substantially the same manner as the embodiment illustrated in FIG. 4, with the added convenience provided by the greater mechanical strength and unitary construction of the syringe body 310.

What is claimed is:
1. An apparatus for injecting fluids comprising
a syringe body formed to define a syringe cavity, the syringe body being formed to have both a fluid port and a vacuum port opening into the syringe cavity, a piston positioned for reversible movement in the syringe cavity between the fluid port and the vacuum port, with the syringe body and the piston defining a first cavity positioned between the piston and the fluid port and a second cavity positioned between the piston and the vacuum port, and with the piston forming an airtight seal with the syringe body to prevent fluid communication between the first cavity and the second cavity and promote movement of the piston toward the vacuum port in response to a decrease in fluid pressure of fluid contained in the second cavity relative to fluid pressure of fluid contained in the first cavity.

a resilient element positioned to connect the piston and the syringe body, the resilient element being deformable in response to movement of the piston toward the vacuum port to provide a store of mechanical energy, a valve for controlling flow into the second cavity from a third port unconnected to the fluid port for equalizing fluid pressures in the first and second cavities to release the store of mechanical energy to drive the piston toward the fluid port and expel fluid contained in the first cavity through the fluid port.

2. The apparatus of claim 1 wherein the resilient element comprises a compressible spring disposed in the second cavity to connect the syringe body and the piston.

3. The apparatus of claim 2 wherein the compressible spring comprises a helical spring having a longitudinal axis extending along the direction of movement of the piston toward the vacuum port, the helical spring being substantially non-deformed when the piston is positioned adjacent to the fluid port and being increasingly deformed as the piston moves toward the vacuum port to provide the store of mechanical energy.

4. The apparatus of claim 1 wherein the syringe body is coupled to a valve body formed to define a connecting passageway coupled in fluid communication with the second cavity through the vacuum port defined in the syringe body.

5. The apparatus of claim 4 wherein a rotary valve is positioned within the valve body to control fluid flow within the connecting passageway.

6. An apparatus for injecting fluids comprising a syringe body formed to define a syringe cavity, the syringe body being formed to have both a fluid port and a vacuum port opening into the syringe cavity, a piston positioned for reversible movement in the syringe cavity between the fluid port and the vacuum port, with the syringe body and the piston defining a first cavity positioned between the piston and the fluid port and a second cavity positioned between the piston and the vacuum port, and with the piston forming an airtight seal with the syringe body to prevent fluid communication between the first cavity and the second cavity and promote movement of the piston toward the vacuum port in response to a decrease in fluid pressure of fluid contained in the second cavity relative to fluid pressure of fluid contained in the first cavity, a resilient element positioned to connect the piston and the syringe body, the resilient element being deformable in response to movement of the piston toward the vacuum port to provide a store of mechanical energy, and means for equalizing fluid pressures in the first and second cavities to release the store of mechanical energy to drive the piston toward the fluid port and expel fluid contained in the first cavity through the fluid port, wherein the syringe body is coupled to a valve body formed to define a connecting passageway coupled in fluid communication with the second cavity through the vacuum port defined in the syringe body, wherein a rotary valve is positioned within the valve body to control fluid flow within the connecting passageway, wherein the valve body defines a cylindrical opening extending therethrough and intercepting the connecting passageway, and a cylindrical rotor having a first valve passageway and a second valve passageway extending therethrough at predefined skew angles relative to each other is positioned within the cylindrical opening in snug slidable fit so that the rotor can be moved between a first valve position with the first valve passageway in fluid communication with the connecting passageway to allow withdrawal of fluid from the second cavity, a second valve position with the second valve passageway in fluid communication with the connecting passageway to allow admission of fluid into the second cavity to equalize fluid pressures in the first and second cavities, and a closed position to prevent fluid transfer both into and out of the second cavity.

7. The apparatus of claim 6 wherein the rotor is connected to a thumb actuated lever to allow one-handed operation of the rotary valve.

8. An apparatus for injecting fluids comprising a syringe body formed to define a syringe cavity, the syringe body being formed to have both a fluid port and a vacuum port opening into the syringe cavity, a piston positioned for reversible movement in the syringe cavity between the fluid port and the vacuum port, with the syringe body and the piston defining a first cavity positioned between the piston and the fluid port and a second cavity positioned between the piston and the vacuum port, and with the piston forming an airtight seal with the syringe body to prevent fluid communication between the first cavity and the second cavity and promote movement of the piston toward the vacuum port in response to a decrease in fluid pressure of fluid contained in the second cavity relative to fluid pressure of fluid contained in the first cavity, a resilient element positioned to connect the piston and the syringe body, the resilient element being deformable in response to movement of the piston toward the vacuum port to provide a store of mechanical energy, and means for equalizing fluid pressures in the first and second cavities to release the store of mechanical energy to drive the piston toward the fluid port and expel fluid contained in the first cavity through the fluid port, a second syringe body formed to define a second syringe cavity, a second piston positioned for reversible movement in the second syringe cavity, and means for rigidly coupling the second piston to the piston to drive the second piston in response to movement of the piston.

9. The apparatus of claim 8 further comprising a connector rigidly coupling the syringe body and the second syringe body.

10. The apparatus of claim 9 wherein the connector includes an air vent in fluid communication with the first cavity of the syringe to allow admission and expulsion of air from the first cavity in response to movement of the piston.

11. The apparatus of claim 8 wherein the area presented by the second piston in contact with fluid is less than the area presented by the piston in contact with fluid so that movement of the piston provides a mechanical advantage for movement of the second piston.

12. An apparatus for dispensing fluids comprising
a syringe body formed to define a syringe cavity, the syringe body being formed to have both a fluid port and a vacuum port opening into the syringe cavity,
a piston positioned for movement in the syringe cavity between the fluid port and the vacuum port, with the syringe body and the piston defining a first cavity positioned between the piston and the fluid port and a second cavity positioned between the piston and the vacuum port,
means for sealing the piston and the syringe body to prevent fluid communication between the first cavity and the second cavity and promote movement of the piston toward the vacuum port in response to a decrease in fluid pressure of fluid contained in the second cavity relative to fluid pressure of fluid contained in the first cavity,
a compression spring connecting the syringe body and the piston,
a first valve mechanism in fluid connection with the second cavity, the valve mechanism having an open position to permit withdrawal of fluid from the second cavity and compress the spring between the piston and syringe body as the piston moves toward the vacuum port in response to withdrawal of fluid from the second cavity, and
a second valve mechanism in fluid communication with the second cavity, the second valve mechanism having an open position to provide fluid communication into the second cavity to equalize fluid pressures in the first and second cavities and allow extension of the compressed spring, with the extension of the spring moving the piston toward the fluid port to expel fluid contained in the first cavity through the fluid port.

13. The apparatus of claim 12 wherein the the first valve mechanism and the second valve mechanism are defined in a dual port valve connected to the syringe body, the dual port valve having both a vacuum line connection and an air inlet that can be respectively brought into fluid communication with a connecting passageway defined in the dual port valve to lie in fluid communication with the second cavity through the vacuum port defined in the syringe body.

14. The apparatus of claim 13 wherein the dual port valve includes a valve body having a cylindrical opening extending therethrough and intercepting the connecting passageway, and a cylindrical rotor having a first valve passageway and a second valve passageway extending therethrough at predefined skew angles relative to each other is positioned within the cylindrical opening in snug slidable fit so that the rotor can be moved between a first valve position with the first valve passageway providing fluid communication between the connecting passageway and the vacuum line connection to allow withdrawal of fluid from the second cavity, a second valve position with the second valve passageway providing fluid communication between the connecting passageway and the air inlet to allow admission of air into the second cavity to equalize fluid pressures in the first and second cavities, and a closed position to prevent fluid transfer both into and out of the second cavity.

15. The apparatus of claim 12 comprising
a second syringe body formed to define a second syringe cavity,
a second piston positioned for reversible movement in the second syringe cavity, and
a rod connecting the piston and the second piston, the rod being positioned to extend through the fluid port and into the second syringe cavity to drive the second piston in response to movement of the piston.

16. The apparatus of claim 15 further comprising a connector rigidly coupling the syringe body and the second syringe body, with the connector formed to define an air vent in fluid communication with the first cavity of the syringe to allow admission and expulsion of air from the first cavity in response to movement of the piston.

17. The apparatus of claim 15 wherein the second syringe body is integrally formed in fluid connection with the syringe body.

18. The apparatus of claim 14 wherein the area presented by the second piston in contact with fluid is less than the area presented by the piston in contact with fluid so that movement of the piston provides a mechanical advantage for movement of the second piston.

19. An apparatus for withdrawing and dispensing fluids comprising
a chamber formed to define a cavity having an aperture for introduction and expulsion of fluids,
means for dividing the cavity into first and second cavities respectively having first and second volumes, the dividing means being movable to alternately increase and decrease the first and second volumes of the first and second cavities,
means for removing fluid from the second cavity to promote movement of the dividing means sufficient to increase the volume of the first cavity and reduce the volume of the second cavity,
means for storing energy produced by movement of the dividing means in response to reduction of the volume of the second cavity, and
a valve for controlling flow into the second cavity from a port unconnected to the means for removing for equalizing fluid pressure in the first and second cavities to release energy stored in the storing means and promote movement of the dividing means in the cavity of the chamber to reduce the volume of the first cavity and increase the volume of the second cavity, so that fluid contained in the first cavity is expelled from the first cavity.

20. A method for injecting fluids comprising the steps of
providing a chamber defining a cavity, the cavity being divided into first and second cavities by a divider situated to prevent fluid communication between the first and second cavities, reducing pressure in the second cavity to create a pressure imbalance between fluid in the first cavity and fluid in the second cavity, storing energy resulting from the pressure imbalance, equalizing the pressure imbalance between the fluid in the first cavity and the fluid in the second cavity by controlling fluid from a source into the second cavity, and applying the stored energy to decrease the volume of the second cavity and expel fluid contained in the first cavity.

21. A system for injecting and aspirating fluids comprising a vacuum source, a fluid source, a syringe body formed to define a syringe cavity, the syringe body being formed to have both a fluid port and a vacuum port opening into the syringe cavity, a piston positioned for reversible movement in the syringe cavity between the fluid port and the vacuum port, with the syringe body and the piston defining a first cavity positioned between the piston and the fluid port and a second cavity positioned between the piston and the vacuum port, and with the piston forming an airtight seal with the syringe body to prevent fluid communication between the first cavity and the second cavity and promote movement of the piston toward the vacuum port in response to a decrease in fluid pressure of fluid contained in the second cavity relative to fluid pressure of fluid contained in the first cavity, a resilient element positioned to connect the piston and the syringe body, the resilient element being deformable in response to movement of the piston toward the vacuum port to provide a store of mechanical energy, means for equalizing fluid pressures in the first and second cavities to release the store of mechanical energy to drive the piston toward the fluid port and expel fluid contained in the first cavity through the fluid port, first and second one-way valves configured to allow fluid flow in only one direction, with the first one-way valve connected between a second fluid port and the fluid port to only allow fluid flow from the fluid port to the second fluid port, and with the second one-way valve connected to the fluid source to only allow fluid flow from the fluid source to the fluid port so that fluid can be drawn into the first cavity from the fluid source and expelled from the first cavity through the second fluid port, and a second valve having an open and a closed position, the second valve being connected in fluid communication with the second fluid port and the vacuum source when the second valve is in its open position so that fluid can be aspirated through the second fluid port.

22. The apparatus of claim 21 wherein the resilient element comprises a compressible spring disposed in the second cavity to connect the syringe body and the piston.

23. The apparatus of claim 22 wherein the compressible spring comprises a helical spring having a longitudinal axis extending along the direction of movement of the piston toward the vacuum port, the helical spring being substantially non-deformed when the piston is positioned adjacent to the fluid port and being increasingly deformed as the piston moves toward the vacuum port to provide the store of mechanical energy.

24. The apparatus of claim 21 wherein the syringe body is coupled to a valve body formed to define a connecting passageway coupled in fluid communication with the second cavity through the vacuum port defined in the syringe body.

* * * * *

UNITED STATES PATENT AND TRADEMARK OFFICE
CERTIFICATE OF CORRECTION

PATENT NO. : 5,176,642

DATED : January 5, 1993

INVENTOR(S) : Thomas P. Clement

It is certified that error appears in the above-identified patent and that said Letters Patent is hereby corrected as shown below:

On the title page, item [54] and in column 1, line 2, in the title change "POWDERED" to --POWERED--.

Signed and Sealed this

Twenty-sixth Day of April, 1994

*Attest:*

BRUCE LEHMAN

*Attesting Officer*  *Commissioner of Patents and Trademarks*